United States Patent [19]
Yokoyama et al.

[11] Patent Number: 5,633,099
[45] Date of Patent: May 27, 1997

[54] CARBONATE COMPOUNDS, NON-AQUEOUS ELECTROLYTIC SOLUTIONS AND BATTERIES COMPRISING NON-AQUEOUS ELECTROLYTIC SOLUTIONS

[75] Inventors: Keiichi Yokoyama; Akio Hiwara, both of Sodegaura; Shigeru Fujita, Kitashinagawa; Atsuo Omaru, Koriyama, all of Japan

[73] Assignees: Mitsui Petrochemical Industries, Ltd.; Sony Corporation, both of Tokyo, Japan

[21] Appl. No.: 461,419

[22] Filed: Jun. 5, 1995

Related U.S. Application Data

[62] Division of Ser. No. 153,429, Nov. 16, 1993.

[30] Foreign Application Priority Data

Nov. 18, 1992 [JP] Japan .................... 4-309041
Nov. 18, 1992 [JP] Japan .................... 4-309042

[51] Int. Cl.$^6$ .................... H01M 10/40
[52] U.S. Cl. .................... 429/194; 429/198; 429/199; 252/62.2
[58] Field of Search .................... 429/194, 198, 429/199, 197; 252/62.2

[56] References Cited

U.S. PATENT DOCUMENTS 4,306,947 12/1981 Bell .
5,382,704 1/1995 Krespan et al. .................... 568/683
5,451,477 9/1995 Omaru et al. .................... 429/218

FOREIGN PATENT DOCUMENTS 2148665 11/1988 Japan .
4104468 8/1990 Japan .

OTHER PUBLICATIONS

Chemical Abstracts, vol. 113, No. 23, 3 Dec. 1990, Columbus Ohio abstract No. 211176b . . . p. 691 & J. Prakt.Chemie vol. 332, No. 3, 1990.
Patent Abstracts of Japan vol. 014, No. 394 (E–0969) 24 Aug. 1990 & JP–A–02 148 665 (Matsushita Electric Ind. Co.) 7 Jun. 1990.
Patent Abstracts of Japan vol. 013, No. 339 (C–624) 31 Jul. 1989 & JP–A–01 117 838 (Neos Co Ltd) 10 May 1989.

*Primary Examiner*—Stephen Kalafut
*Assistant Examiner*—Carol Chaney
*Attorney, Agent, or Firm*—Sherman and Shalloway

[57] ABSTRACT

A novel carbonate compound represented by the general formula [I]:

$$R^3CH_2O\text{-}CO\text{-}OCH_2R^4 \qquad [I]$$

wherein $R^3$ represents an alkyl group or an alkyl group substituted with one or more halogen atoms, and $R^4$ represent an alkyl group having no hydrogen atom at the β-position thereof or an alkyl group substituted with one or more halogen atoms having no hydrogen atom at the β-position thereof, with the proviso that $R^3$ is not identical to $R^4$, which has excellent properties as solvent, is disclosed. A non-aqueous electrolytic solution and a battery utilizing the novel carbonate compound are also disclosed.

24 Claims, 14 Drawing Sheets

Example 1

Example 2

Example 2

Example 4

Example 4

Example 5

Example 5

Example 6

Example 6

CARBONATE COMPOUNDS, NON-AQUEOUS ELECTROLYTIC SOLUTIONS AND BATTERIES COMPRISING NON-AQUEOUS ELECTROLYTIC SOLUTIONS

This is a division of application Ser. No. 08/153,429 filed Nov. 16, 1993.

BACKGROUND OF THE INVENTION

1. Field of the Invention

The present invention relates to novel asymmetric carbonate compounds and, more specifically, It relates to novel carbonate compounds useful as solvents having excellent anti-oxidation properties, starting materials for various organic synthesis, pharmaceuticals, agricultural chemicals and the like.

The present invention further relates to a non-aqueous electrolytic solution comprising carbonate compounds and a non-aqueous electrolyte battery utilizing the solution.

2. Related Art

The term "carbonate compound" herein used means a diester compound of carbonic acid represented by the formula R-O-CO-O-R'. As such a carbonate compound, generally known are symmetric carbonate compounds such as dimethyl carbonate and diethyl carbonate, and cyclic carbonate compounds such as ethylene carbonate and propylene carbonate. These carbonate compounds are used as special solvents In the fields of pharmaceutical chemistry, agricultural chemistry and the like. And these carbonates are also used as starting materials and intermediates of dyes, plant protective agents, synthetic resins, pharmaceuticals, agricultural chemicals, and the like (for example, Japanese Patent Application Laid-open (KOKAI) Nos. 54-125617 and 54-63023). Further, it has been reported that electrolyte solvents comprising cyclic carbonate compounds are utilized for non-aqueous batteries containing alkali metals, alkaline earth metals or compounds containing these metals as cathode active materials, because of its high dielectric constant and good solubility as to inorganic materials of the carbonate compounds.

Though fluorine-containing carbonate compounds are not known well, some of such carbonate compounds have been reported an examples thereof are di-trifluoroethyl carbonates as starting materials of synthetic resins (U.S. Pat. No. 4,349,486), di-hexafluoroisopropyl carbonate and ethyl hexafluoroisopropyl carbonate as agricultural chemicals (U.S. Pat. No. 3,359,296), di(perfluorophenyl) carbonate as flame-retardants (U.S. Pat. No. 4,102,912) and the like.

Symmetric carbonate compounds are generally synthesized by a reaction of phosgen and an alcohol. On the other hand, for the synthesis of asymmetric carbonate compounds, it is necessary to introduce two alkoxy groups, and as the method for the synthesis of such carbonate compounds, there have been proposed a method by a reaction of a carbamate and an alcohol (Japanese Patent Application Laid-open (KOKAI) No. 57-26645), a method by allowing an alcohol to react with a chloroformate and the like.

Meanwhile, it is basically required for organic solvents to be able to dissolve organic materials and, in addition, they must be chemically and physically stable, can be a liquid state in a wide temperature range, have a low viscosity and have a high flash point, i.e., be difficult to catch fire. Further, depending on the purposes for which the solvents are used, it is also Important that they have a high dielectric constant.

While ordinary organic solvents such as benzene, methanol and acetone generally have a low flash point and easily catch fire, the above described carbonate compounds have a relatively high flash point. For example, the flash points of dimethyl carbonate and diethyl carbonate are 22° and 25° C., respectively and hence they do not easily catch fire. Moreover, they have excellent properties as a solvent, for example, they can dissolve organic materials sufficiently, are chemically and physically stable and have a high dielectric constant. For these reasons, there are already proposed electrolyte solvents for batteries comprising carbonate compounds (Japanese Patent Application Laid-open (KOKAI) No. 61-64082).

As described above, the symmetric carbonate compounds whose alkyl groups consisting of carbon atoms and hydrogen atoms have more excellent properties as compared with the ordinary solvents. However, it cannot be said that they have sufficient characteristics for certain uses where the solvents are required to have chemical and physical stability, high flash point and high flame retardant properties such as uses in batteries, and electrolytic solutions for electrochemical reactions. In addition, compounds having a symmetric structure are generally prone to crystallize and have a relatively high melting point despite the low molecular weight (e.g., dimethyl carbonate has a melting point of 3° to 4° C.), and this leads to a drawback that the temperature range where they can be used as a liquid is limited.

The object of the present invention is to provide novel asymmetric carbonate compounds and, more specifically, the object of the present invention is to provide novel carbonate compounds which are chemically and physically stable, have a high dielectric constant, can sufficiently dissolve organic and inorganic materials and, further, useful as solvents having a high flash point and a low melting point.

Electric cells utilizing non-aqueous electrolytic solution have been conventionally and widely used as electric sources of various kinds of consumer electronic equipments because of their reliability such as storage characteristics. However, non-aqueous electrolytic solutions generally have electro-conductivity tens to hundreds times lower than aqueous electrolytic solutions and, in particular, non-aqueous electrolytic solutions having low decomposition voltage show poor charge/discharge cycle characteristics and short life-time in batteries. Further, non-aqueous electrolytic solution have another drawback, that is, when charge/discharge cycles are repeated in a non-aqueous electrolyte battery, needlelike metals, so-called "dendrites", are occasionally deposited and they are prone to be released from electrodes to form reactive metal powder, or to penetrate the separator separating the cathode and the anode to cause short circuit.

In order to improve the electro-conductivity of non-aqueous electrolytic solutions, it have been proposed that a low-viscosity solvent such as dimethoxyethane, tetrahydrofuran and 1,3-dioxoran is added to a solvent having a high dielectric constant such as propylene carbonate, γ-butyrolactone and sulfolane (for example, Denki Kagaku (Electrochemistry), 53, No. 3, p.173 (1985)). Further, it have also been proposed to, as attempts to improve the durability of electrolytic solutions, use a carbonate having a high decomposition voltage such as diethyl carbonate instead of a solvent having a low decomposition voltage such as dimethoxyethane to improve the battery charge/discharge efficiency (for example, Japanese Patent Application Laid-open (KOKAI) No. 2-10666), or add a phosphate to electrolytic solutions to make the solutions self-extinguishing (Japanese Patent Application Laid-open (KOKAI) No. 4-184870).

Meanwhile, because batteries having a high energy density are desired, various researches concerning high voltage batteries are being conducted. For example, researches have been conducted as to a battery comprising a cathode of complexed oxide of lithium and transition metal such as $LiCoO_2$, $LiNiO_2$ and $LiMn_2O_4$ and an anode of metallic lithium, lithium alloys or a lithium/carbon compound and capable of generating voltage of 4 V. In such a battery, decomposition of electrolytic solutions due to oxidation become likely to occur and, therefore, conventionally used esters such as γ-butyrolactone and ethyl acetate and ethers such as 1,3-dioxoran, tetrahydrofuran and dimethoxyethane are not preferred solvents since they have a low decomposition voltage and react with the cathode and, when such a conventional solvent is used in the battery of this type, it has further drawbacks, for example, the battery capacity is reduced every charge/discharge cycle and gas Is generated to elevate the internal pressure of the battery. Therefore, electrolyte solvents having anti-oxidation properties have been desired.

When metallic lithium, a lithium alloy or a complexed oxide Is used for the anode of the battery, metallic lithium deposited during the charging or deposited due to overcharging is highly reactive and there is possibility that it reacts even with a electrolyte solvent excellent in anti-oxidation properties. Further, another drawback of batteries of this type has been pointed out from the viewpoint of use, that is, when charge/discharge cycles are repeated in the battery, needlelike lithium crystals, so-called "dendtrite", are occasionally deposited and they are prone to be released from electrodes to form reactive lithium powder or to penetrate the separator which separating the cathode and the anode to cause short circuit.

The present invention has been completed to solve the above described problems and its object is to provide a non-aqueous electrolytic solution, which is excellent in decomposition voltage and charge/discharge cycle characteristics and has a high flash point, i.e., which is suitable for an electrolyte solvent. Further, it is also the object of the present invention to provide a non-aqueous electrolyte battery which is capable of generating high voltage and excellent in battery characteristics.

DETAILED DESCRIPTION OF THE INVENTION

As a result of our researches conducted in order to achieve the above objects, we found that the chemical stability of carbonate compounds can be improved and the flash point is elevated by introducing a substituent into at least one of the alkyl groups of the carbonate compounds at the β-position thereof and that the melting point is lowered by making the structure asymmetric and have completed the present invention. That is, the asymmetric carbonate compounds according to the present invention are those carbonate compounds represented by the following general formula [I]:

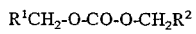
 [I]

herein $R^1$ represents a hydrogen atom, an alkyl group or an alkyl group substituted with one or more halogen atoms and $R^2$ represents an alkyl group having no hydrogen atom at the α-position thereof or an alkyl group substituted with one or more halogen atoms and having no hydrogen atom at the α-position thereof with a proviso that $R^1$ is not Identical to $R^2$.

The group of $R^1$ is preferably an alkyl group or an alkyl group substituted with one or more halogen atoms having 1 to 4 carbon atoms and, as examples of such a preferred group, there can be mentioned methyl group, ethyl group, propyl group, butyl group and those groups constituted by the foregoing alkyl groups of which hydrogen atoms are partially or totally substituted by halogen atoms.

The group of $R^2$ is preferably an alkyl group having 4 to 7 carbon atoms and not having a hydrogen atom at the α-position thereof and, as examples of such a preferred group, there can be mentioned branched alkyl groups such as t-butyl group and —$C(CH_2CH_3)_3$. The halogen atom-substituted alkyl group preferably has 1 to 4 carbon atoms and is a linear group. The halogen atoms may be fluorine, chlorine, bromine or iodine. In particular, a fluorine atom-substituted alkyl group is preferred. As examples of the fluorine atom-substituted alkyl group, there can be mentioned fluoromethyl group, fluoroethyl group, fluoropropyl group, fluorobutyl group and the like. Though the number of the halogen atoms contained in the halogen atom-substituted alkyl group is not particularly limited, it is preferred that at least the hydrogen atoms at the α-position thereof are substituted by halogen atoms. Examples of the preferred halogen atom-substituted alkyl group include trifluoromethyl group, tetrafluoroethyl group, pentafluoroethyl group and heptafluoropropyl group.

Specific examples of the compounds represented by the formula [I] are methyl neopentyl carbonate, methyl 2,2,2-triethylethyl carbonate, methyl 2,2,2-trifluoroethyl carbonate, methyl 2,2,2-trichloroethyl carbonate, methyl 2,2,2-tribromoethyl carbonate, methyl 2,2,2-triiodoethyl carbonate, ethyl 2,2,2-trifluoroethyl carbonate, methyl 2,2,3,3,3-pentafluoropropyl carbonate, methyl 2,2,3.3-tetrafluoropropyl carbonate, methyl 2,2,3,3,4,4,4-heptafluorobutyl carbonate and 2,2,2-trifluoroethyl 2,2,3,3,3-pentafluoropropyl carbonate.

When the carbonate compounds of the present invention are used as a solvent, they preferably have a hydrogen atom, a methyl group (—$CH_3$) or a trifluoromethyl group (—$CF_3$) as the group of $R^1$ and a t-butyl group or a trifluoromethyl group as the group of $R^2$. More preferably, they have a hydrogen atom or a methyl group as the group of $R^1$ and a trifluoromethyl group as the group of $R^2$.

The carbonate compounds of the present invention are chemically stable, in particular, show excellent oxidation resistance, do not react with water as they are, are not oxidized even if they are left in air and do not react with metallic lithium. Further, they are soluble in ethanol, ether, acetone and toluene and therefore they can be used as a solvent for various reaction operations, washing or cleaning solvents or the like.

In addition, because of the high dielectric constant of the carbonate compounds according to the present invention, they have properties that they can dissolve not only organic materials such as ester compounds and carboxylic acids but also metal salts such as lithium hexafluorophosphate, lithium hexafluoroarsinate, lithium tetrafluoroborate, lithium trifluoromethanesulfonate, lithium perchlorate. Moreover, the carbonate compounds of the present invention are also physically stable, that is, they are not easily pyrolyzed, have a high flash point and flame retardant properties, and do not easily undergo electrochemical reduction or oxidation reaction. Therefore, they are suitably used as an electrolyte solvent for batteries, and for electrochemical reactions and the like.

The carbonate compounds of the present invention can be synthesized through an transesterification reaction represented by the following reaction formula using a corresponding alcohol and a dialkyl carbonate such as dimethyl carbonate in the presence of a basic catalyst such as sodium methoxide and sodium hydroxide.

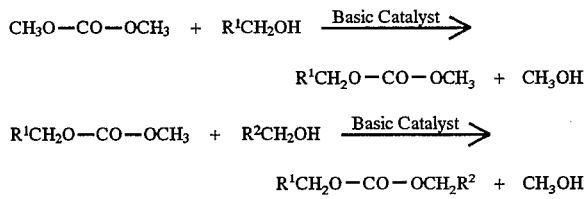

As the basic catalyst used for the synthesis of the carbonate compounds of the present invention through the transesterification reaction of a carbonate and a monohydroxy alcohol, the carbonate of the alkali metal represented by $M_2CO_3$ (where M is alkali metal atom), in particular, may be used. These catalysts are stable and enable to form the carbonate with a high selectivity. Examples of the catalyst are sodium carbonate, potassium carbonate, lithium carbonate etc. and potassium carbonate is, in particular, preferred. The alkali metal carbonate is used in any shape such as powder, granules, spherical shape or cylindrical shape, but particle size thereof is preferably 0.1–10 mm. The amount of the catalyst is usually in the range of the molecular rate of $10^{-5}$ to $10^{-1}$, preferably $10^{-4}$ to $10^{-2}$.

The carbonate compounds of the present invention are preferably prepared by the transesterification reaction described above, but they can be also prepared by a method where a chloroformate is reacted with an alcohol as shown in the following reaction formula, and by a method where a carbamate is reacted with an alcohol or the like.

$$Cl\text{-}CO\text{-}OCH_2R^2 + R^1CH_2OH \rightarrow R^1CH_2O\text{-}CO\text{-}OCH_2R^2$$

The carbonate compounds of the present invention can be used not only as various solvents such as ordinary solvents for organic synthesis, washing or cleaning solvents, solvents for electrochemical reaction and electrolyte solvents for batteries but also as organic synthesis reagents such as halogenoalkylating agents and carbonylating agents, pharmaceuticals, agricultural chemicals and flame-retardant.

The non-aqueous electrolyte and battery of the present invention which utilize the carbonate will be explained hereinafter.

The inventors had eagerly conducted researches in order to produce a non-aqueous electrolyte battery capable of generating high voltage and excellent in battery characteristics, and to provide a electrolytic solution excellent in decomposition voltage and charge/discharge characteristics. As a result, it was found that when a hydrogen atom at the β-position of at least one alkyl group of a carbonate is substituted, the chemical stability and the anti-oxidation properties of the carbonate are improved and the reactivity with metallic lithium of the carbonate is reduced. Further, It was also found that life-time of a battery after charge/discharge cycle was imposed was improved by using an electrolytic solution of the battery comprising a carbonate where a hydrogen atom at the β-position of at least one alkyl group of the carbonate is substituted.

That is, the non-aqueous electrolytic solution of the present invention comprises the carbonate of the general formula [II]:

wherein $R^3$ represents an alkyl group or an alkyl group substituted by one or more halogen atoms and $R^4$ represents an alkyl group having no hydrogen atom at the β-position or an alkyl group substituted by one or more halogen atoms and having no hydrogen atom at the β-position.

The non-aqueous electrolyte battery of the present invention utilizes an electrolytic solution containing the carbonate of the general formula [II] as the electrolytic solution.

In the non-aqueous electrolyte battery of the present invention, as the anode material, metal materials such as metallic lithium and lithium alloys, metal sulfides and various carbon materials can be used, and carbon materials capable of storing and releasing lithium ions are particularly preferred. Such carbon materials may be graphite or amorphous carbon, and all kinds of carbon materials such as activated carbon, carbon fibers, carbon black and mesocarbon microbeads can be used.

As the cathode material, transition metal oxides and sulfides such as $MoS_2$, $TiS_2$, $MnO_2$ and $V_2O_5$, complexed oxides of lithium and transition metal such as $LiCoO_2$, $LiMnO_2$, $LiMn_2O_4$ and $LiNiO_2$ and the like can be used, and the complexed oxides of lithium and transition metal are preferred.

According to the present invention, by using an electrolytic solution containing the carbonate of the general formula [II] as the electrolytic solution, the reactivity with lithium is lowered, the decomposition of the electrolytic solution due to oxidation becomes not likely to occur, the flash point is elevated and the life-time of the battery on which charge/discharge cycle Is imposed, Is elongated.

The non-aqueous solution of the present invention will be explained further in detail hereafter.

In the general formula [II], the group $R^3$ represents an alkyl group or an alkyl group substituted by one or more halogen atoms, preferably having 1 to 5 carbon atoms and $R^4$ represents an alkyl group not having a hydrogen atom at the β-position thereof, preferably having 5 to 8 carbon atoms or an alkyl group substituted by one or more halogen atoms, preferably having 2 to 5 carbon atoms. Examples of the alkyl groups include methyl, ethyl, propyl and isopropyl groups, and examples of the alkyl group not having a hydrogen atom at the β-position thereof include neopentyl (—$CH_2C(CH_3)_3$) and 2,2,2-triethylethyl (—$CH_2C(CH_2CH_3)_3$) groups. As the alkyl group substituted by one or more halogen atoms, those containing halogen atoms of fluorine and chlorine atoms are preferred and those containing fluorine atoms are particularly preferred. Examples of the alkyl group substituted by one or more halogen atoms include 2-fluoroethyl (—$CH_2CFH_2$), 2,2-difluoroethyl (—$CH_2CF_2H$), 2,2,2-trifluoroethyl (—$CH_2CF_3$), 2,2,3,3,3-pentafluoropropyl (—$CH_2CF_2CF_3$), 2,2,3,3-tetrafluoropropyl (—$CH_2CF_2CF_2H$) and 1,1,1,3,3,3-hexafluoroisopropyl group (—$CH(CF_3)_2$).

Specific examples of the carbonate include those carbonates containing an alkyl group not having a hydrogen atom at the β-position such as methyl neopentyl carbonate and methyl 2,2,2-triethylethyl carbonate, and those carbonates containing an alkyl group substituted by one or more halogen atoms such as methyl trichloroethyl carbonate, methyl tribromoethyl carbonate, methyl triiodoethyl carbonate, methyl 2,2,2-trifluoroethyl carbonate, ethyl 2,2,2-trifluoroethyl carbonate, methyl 2,2,3,3,3-pentafluoropropyl carbonate, methyl 2,2,3,3-tetrafluoropropyl carbonate, methyl 1,1,1,3,3,3-hexafluoroisopropyl carbonate, di-2,2,2-trifluoroethyl carbonate, 2,2,2-trifluoroethyl 2,2,3,3,3-pentafluoropropyl carbonate. These carbonates can be used alone or any combination thereof as an electrolytic solution.

The electrolytic solution may be exclusively composed of one or more of the carbonates of the general formula [II], but it may be a mixed solvent with cyclic carbonates such as propylene carbonate, γ-butyrolactone, sulfolane or the like, and thereby the solubility of an electrolyte in the solvent is increased to further improve the electro-conductivity. The cyclic carbonate may be a 5- or 6-membered cyclic carbonate, and 5-membered cyclic carbonates are particularly preferred. Particularly preferred examples of the cyclic carbonate are ethylene carbonate, propylene carbonate, butylene carbonate and vinylene carbonate.

When the carbonate of the general formula [II] is used in a mixed solvent with a cyclic carbonate, the volume ratio of the carbonate of the general formula [II] and the cyclic carbonate may be 1:9 to 9:1, preferably, 2:8 to 8:2. When the ratio Is within the specified range, it is preferably possible to obtain low viscosity and high dielectric constant, and hence, high electro-conductivity.

The solvent for electrolytic solution of the present invention may be optionally added, in addition to the carbonate of the general formula [II] and the cyclic carbonate, with a non-aqueous solvent conventionally used as a solvent for battery electrolytic solution such as ethers and linear carbonates in an amount which does not deteriorate the characteristics of the electrolytic solution solvent of the present invention.

Electrolyte contained in the electrolytic solution comprising the carbonate of the general formula [II] may be an electrolyte used in a conventional electrolyte solution and preferred examples of such an electrolyte Include lithium salts such as $LiPF_6$, $LiBF_4$, $LiClO_4$, $LiAsF_6$, $LiCF_3SO_3$, $LiAlCl_4$, $LiN(SO_2CF_3)_2$, $LiC_4F_9SO_3$ and $LiC_8F_{17}SO_3$. Particularly preferred are $LiPF_6$, $LiBF_4$, $LiCF_3SO_3$ and $LiClO_4$.

The concentration of the electrolyte in the solvent may be usually 0.1 to 3 mol/liter, preferably, 0.5 to 1.5 mol/liter. The non-aqueous electrolyte battery of the present invention comprises the non-electrolytic solution explained above as the electrolytic solution, and its shape or form may be freely selected within the scope of the invention.

EXAMPLES

The present Invention will be further illustrated by referring to the following examples, but the present invention is no way limited by these examples.

EXAMPLE 1

Synthesis of methyl neopentyl carbonate (the compound of the formula [I] where $R^1$=H and $R^2$=t-butyl)

Figure 1:
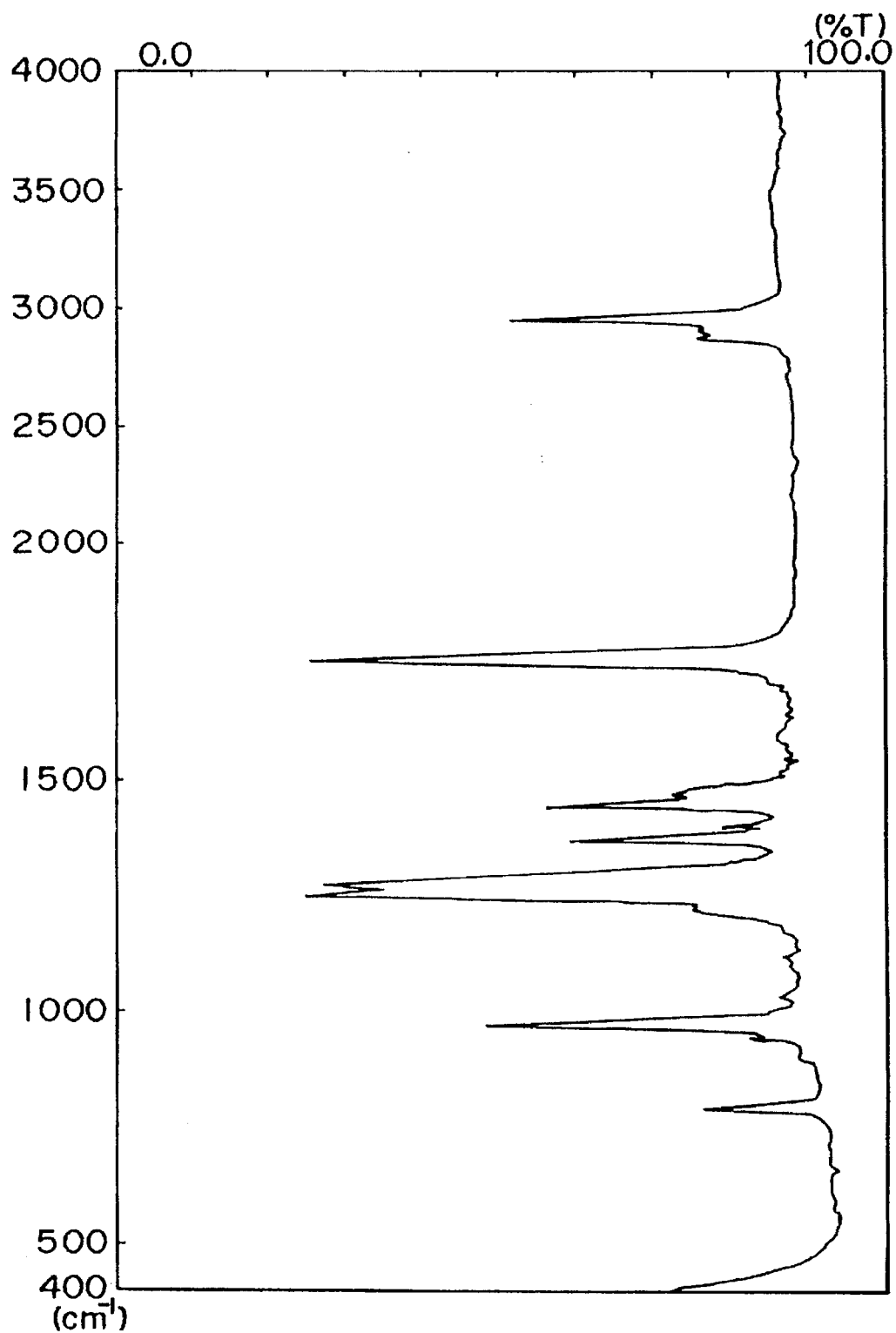
FIGS. 1, 3, 5, 7, 9 and 11 respectively show the IR spectrum of one of the carbonate compounds of the present Invention, the compound of Example 1, 2, 3, 4, 5 and 6 respectively.
Figure 2:
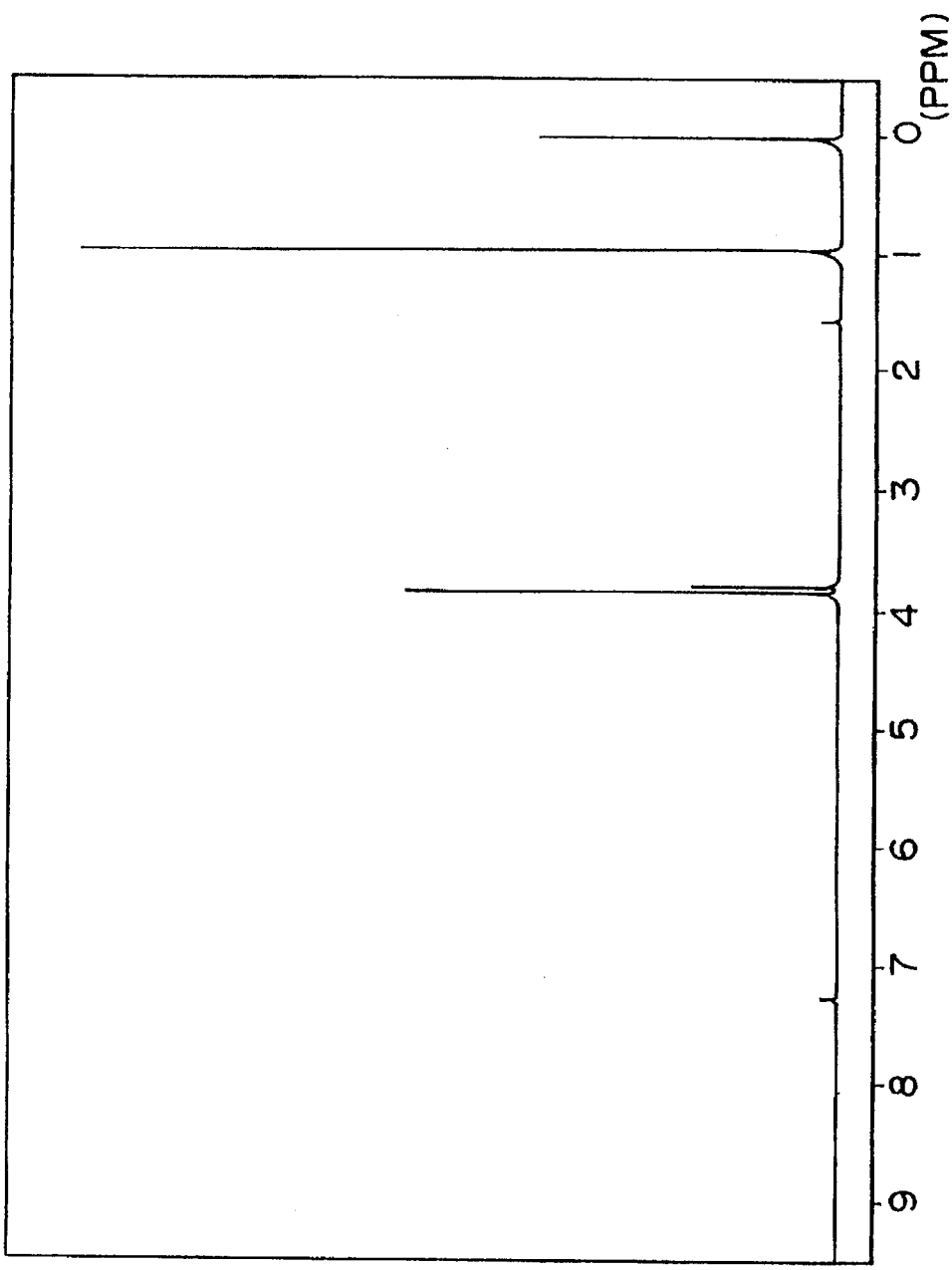
FIGS. 2, 4, 6, 8, 10 and 12 respectively show the NMR spectrum of one of the carbonate compounds of the present invention, the compound of Example 1, 2, 3, 4, 5 and 6 respectively.

To a mixed solution of neopentyl alcohol (500 ml, 5.7 mol) and dimethyl carbonate (2070 g, 23.0 mol), a 28% sodium methoxide/methanol solution (11 g) was added and the mixture was heated to 100° C. to remove the methanol by evaporation for 6 hours. After allowing the mixture to cool to room temperature, an aqueous solution of ammonium chloride was added to the mixture and the mixture was shaken to remove the sodium methoxide. The organic layer was washed with water, dried and distilled to give methyl neopentyl carbonate as a colorless liquid (450 g, yield 55%). The chemical structure of the produced compound was determined based on the IR and NMR absorbance spectra shown in FIG. 1 and FIG. 2 respectively and the mass spectrometry spectrum (M/e=146).

The absorbance peaks of IR and NMR are shown below.

IR (neat): 2958 (C-H), 1443, 1372, 1280, 1260, 937 $cm^{-1}$

NMR ($CDCl_3$ soln., δppm): 0.95 (s, 9H, $C(CH_3)_3$), 3.78 (s, 3H, $OCH_3$), 3.83 (s, 2H, $OCH_3$)

The major physical properties are also shown in Table 1.

EXAMPLE 2

Synthesis of methyl 2,2,2-trifluoroethyl carbonate (the compound of the formula [I] where $R^1$=H and $R^2$=trifluoromethyl)

Figure 3:
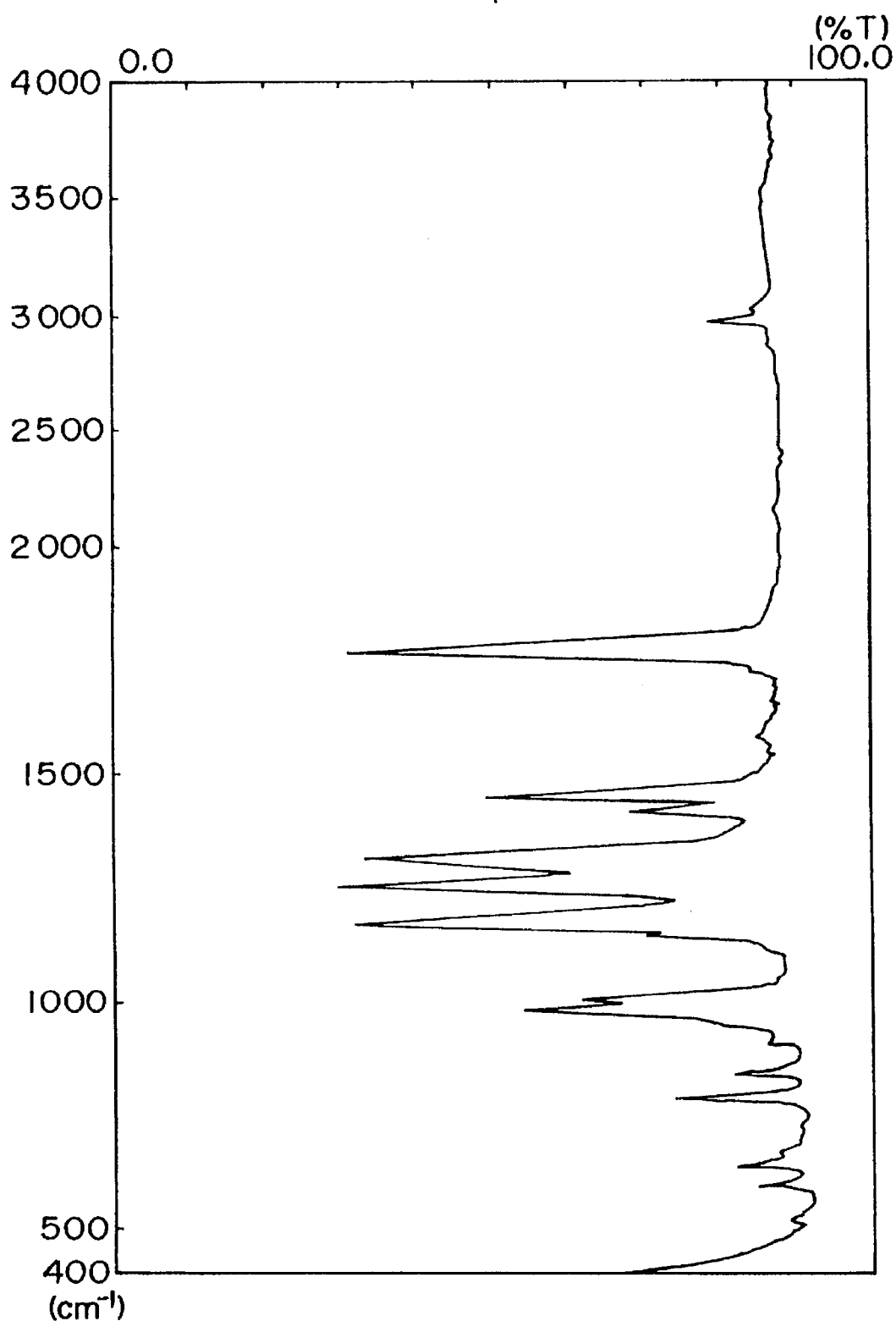
Figure 4:
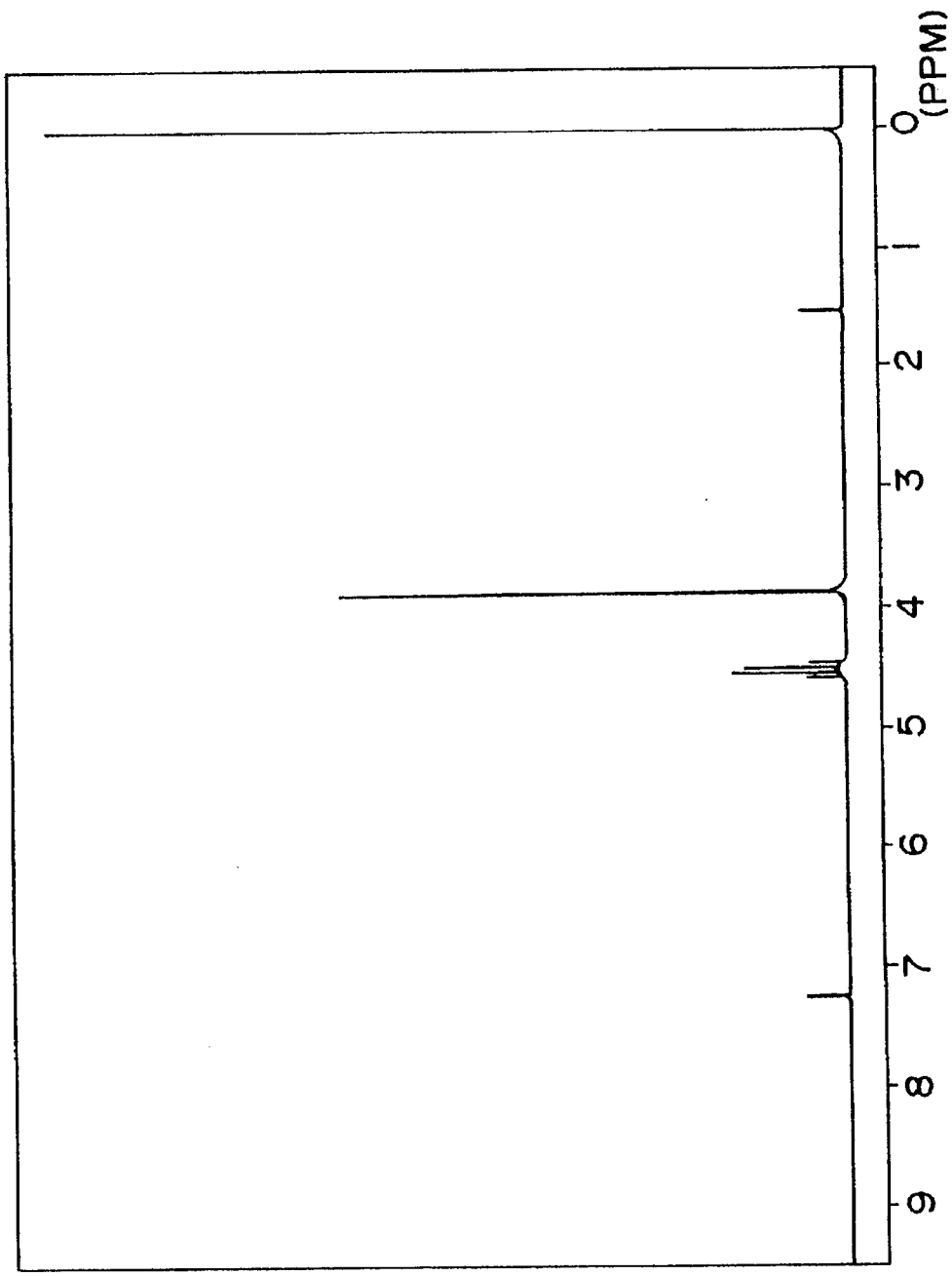

In a flask (3-liter volume) equipped with 10 distillation columns, 2,2,2-trifluoroethanol (790 g, 7.9 ml), dimethyl carbonate (2140 g, 23.7 mol) and a 28% sodium methoxide/methanol solution (15.3 g) were charged. The flask was heated to 100° C. to allow the starting materials to react for 30 hours while removing the methanol from the distillation columns by evaporation. After allowing the mixture to cool to room temperature, an aqueous solution of ammonium chloride was added to the mixture and the mixture was shaken to remove the sodium methoxide. The organic layer was washed with water, dried and distilled to give methyl 2,2,2-trifluoroethyl carbonate as a colorless liquid (410 g, yield 33%). The chemical structure of the produced compound was determined based on the IR and NMR absorbance spectra shown in FIG. 3 and FIG. 4 respectively and the mass spectrometry spectrum (M/e=158).

The absorbance peaks of IR and NMR are shown below.

IR (neat): 2966 (C-H), 1769 (C=O), 1448, 1412, 1317, 1256, 1171, 999, 980, 839, 788, 638, 592 $cm^{-1}$ NMR ($CDCl_3$ soln., δppm): 3.86 (s, 3H, $OCH_3$), 4.40 (q, 2H, J=9 Hz, $OCH_2CF_3$)

The physical properties are also shown in Table 1.

By using the same starting materials and repeating the same procedures as above except that a flask of 5-liter volume with 20 distillation columns was used and that the reaction was carried out at 120° C., methyl 2,2,2-trifluoroethyl carbonate could be obtained with a high yield (710 g, yield 57%).

EXAMPLE 3

Synthesis of ethyl 2,2,2-trifluoroethyl carbonate (the compound of the formula [I] where $R^1$=methyl and $R^2$=trifluoromethyl)

Figure 5:
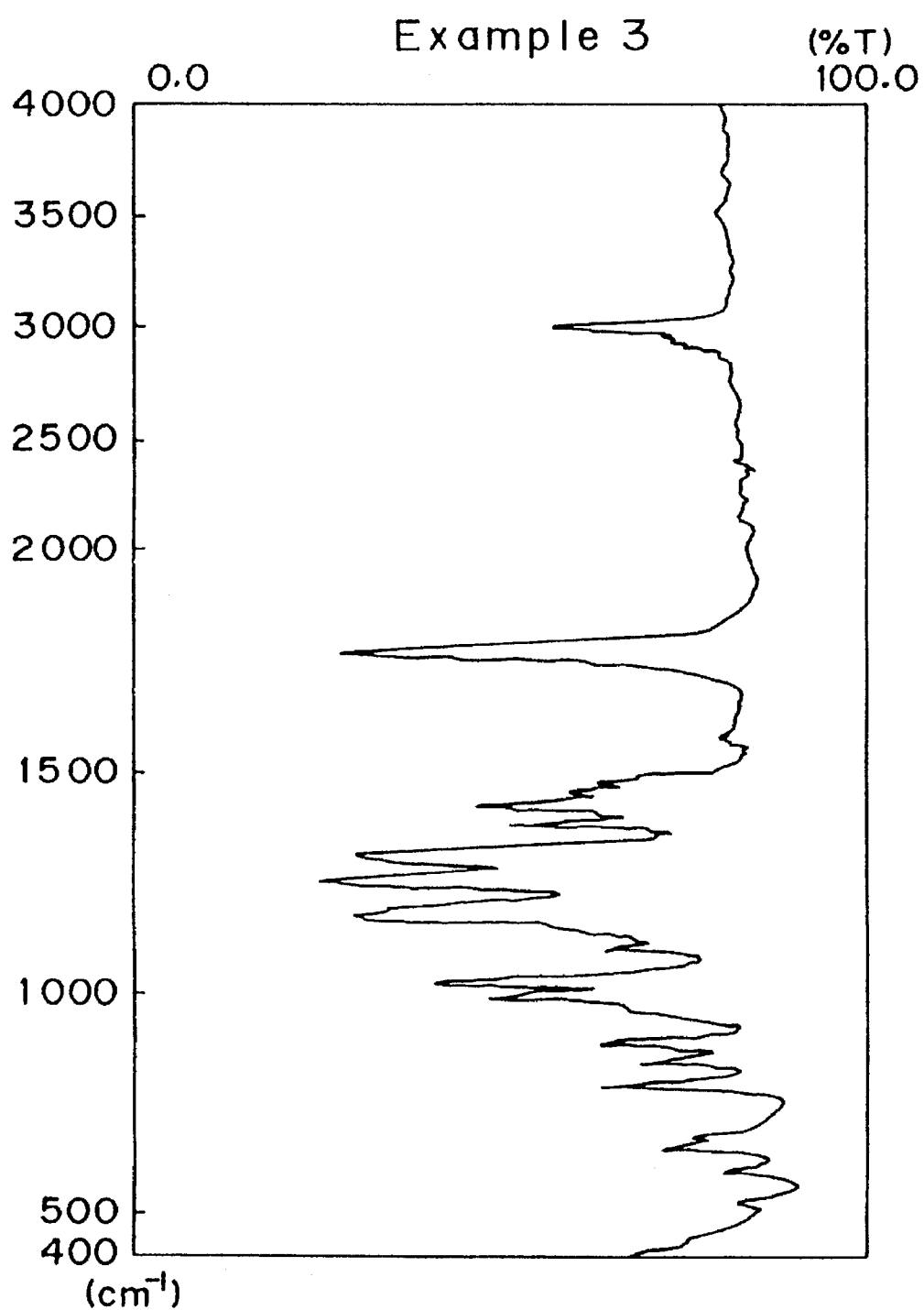
Figure 6:
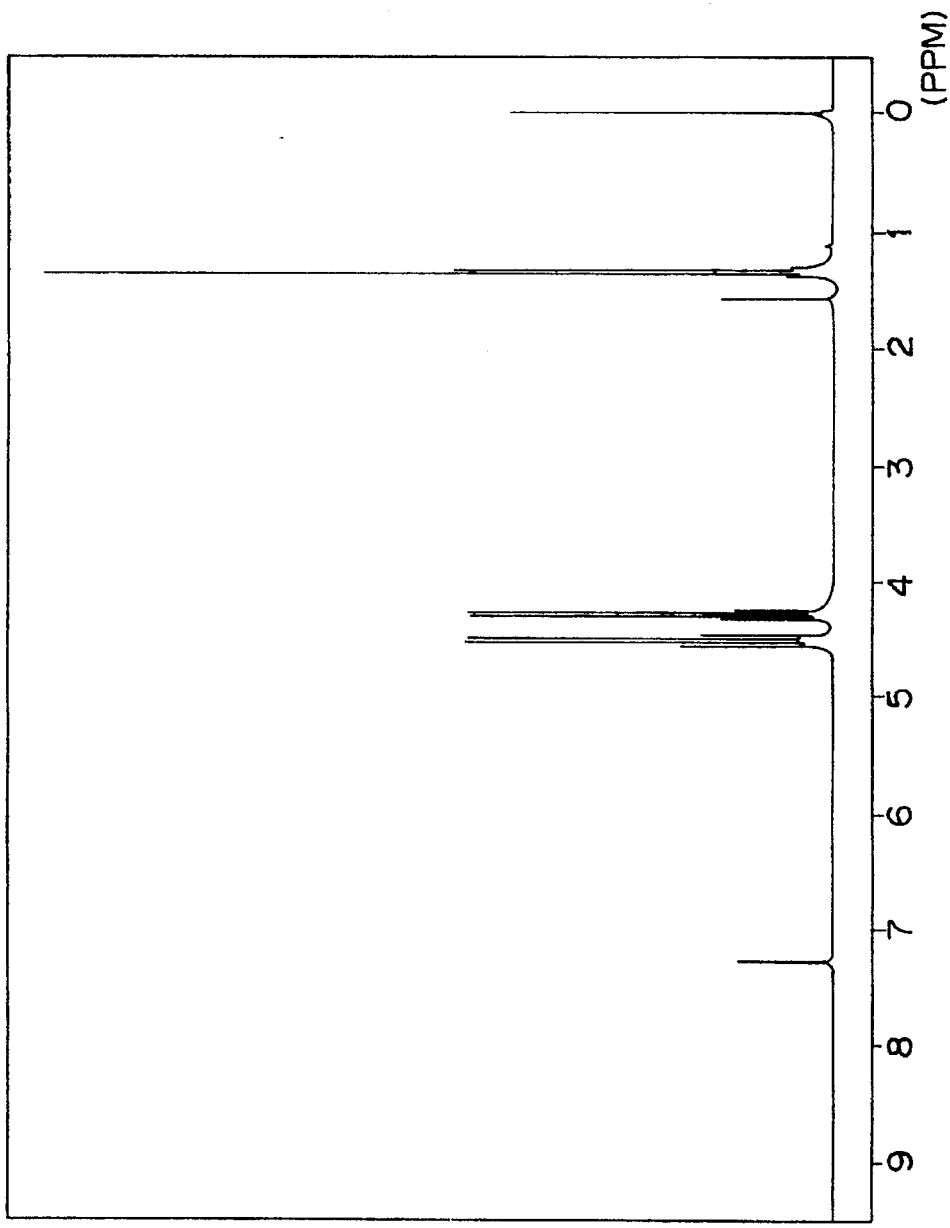

In a flask (5-liter volume), 2,2,2-trifluoroethanol (800 g, 8.0 mol), ethyl chlorocarbonate (867 g, 8.0 mol) and diethyl ether (1000 ml) were charged. While the flask was cooled so that the reaction was carried out at −5° C. to 0° C., a 29.5% by weight aqueous solution of potassium hydroxide (1500 g) was added dropwise to the flask for 6 hours and the mixture was stirred for 12 hours at room temperature. The ether layer was separated, washed with water, dried and distilled to give ethyl 2,2,2-trifluoroethyl carbonate as a colorless liquid (960 g, yield 70%). The chemical structure of the produced compound was determined based on the IR and NMR absorbance spectra shown in FIG. 5 and FIG. 6 respectively and the mass spectrometry spectrum (M/e=172).

The absorbance peaks of IR and NMR are shown below.

IR (neat): 2982 (C-H), 1763 (C=O), 1446, 1415, 1372, 1310, 1246, 1170, 1020, 987, 881, 787, 640, 589 cm$^{-1}$ NMR (CDCl$_3$ soln., δppm): 1.35 (t, 3H, J=8 Hz, OCH$_2$CH$_3$), 4.27 (q, 2H, J=7 Hz, OCH$_2$CF$_3$), 4.50 (q, 2H, J=8 Hz, OCH$_2$CH$_3$)

The major physical properties are also shown in Table 1.

EXAMPLE 4

Synthesis of methyl 2,2,3,3,3-pentafluoropropyl carbonate (the compound of the formula [I] where R$^1$=H and R$^2$=pentafluoroethyl)

Figure 7:
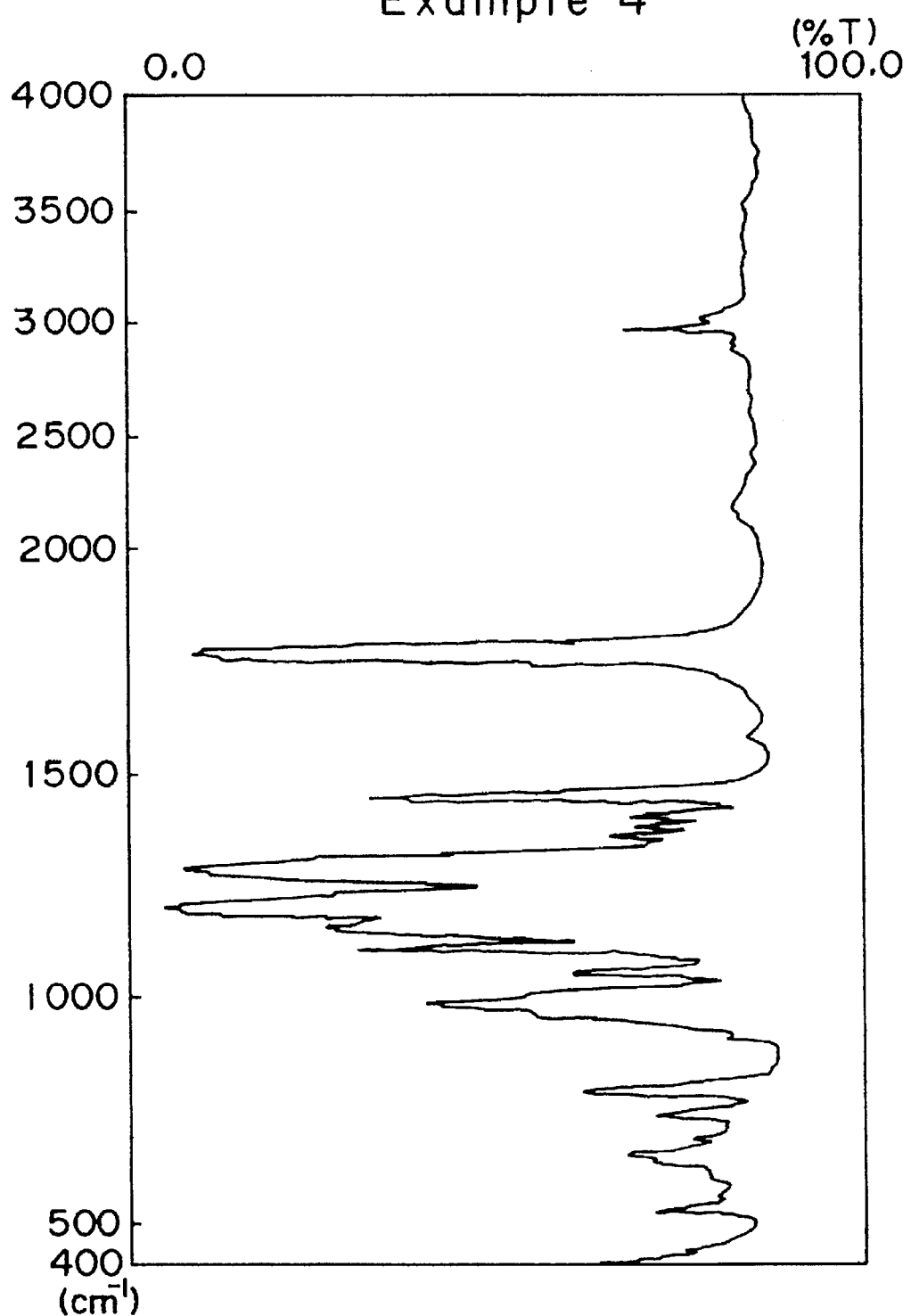
Figure 8:
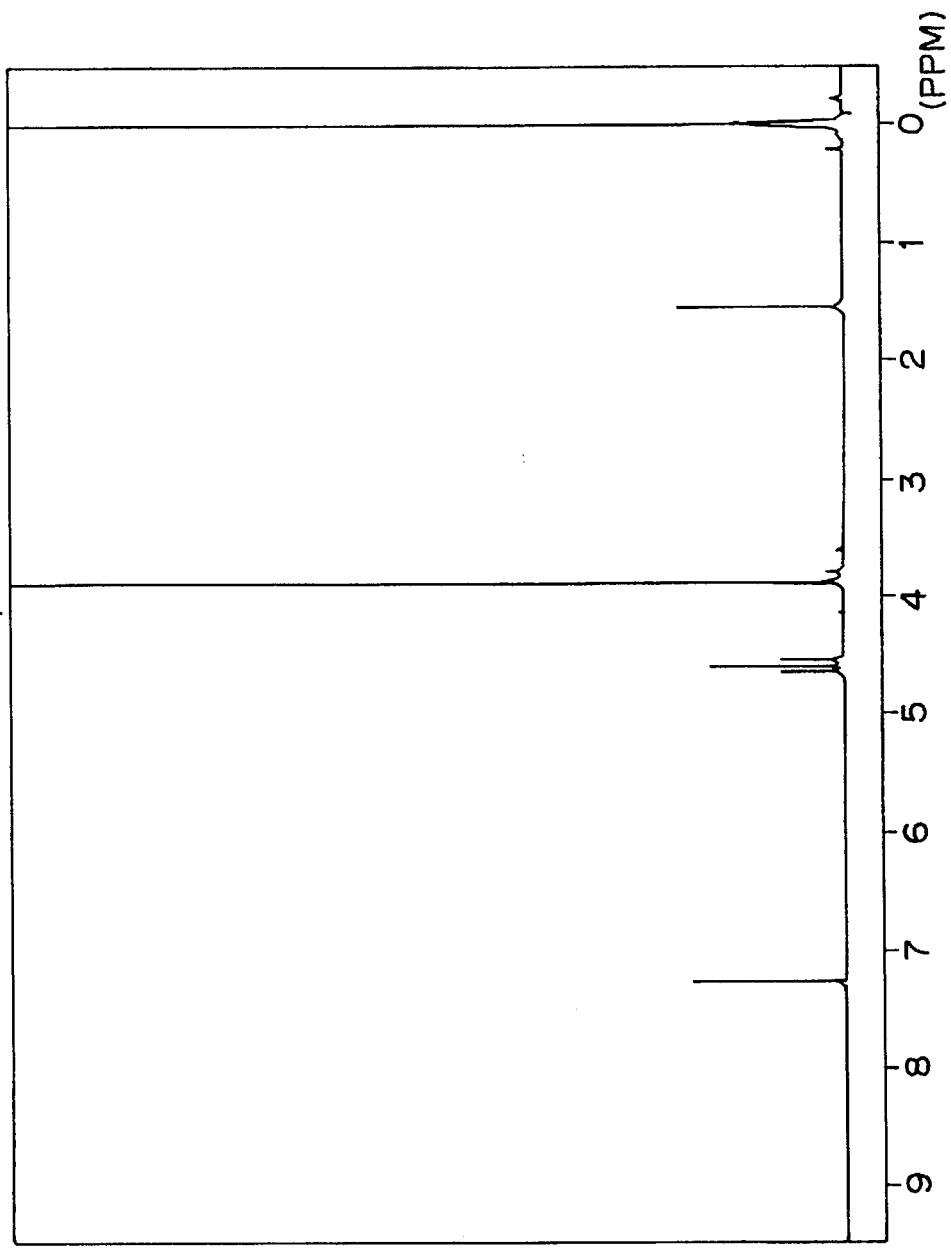

In a flask (500-ml volume) equipped with 10 distillation columns, 2,2,3,3,3-pentafluoropropanol (100 g, 0.67 mol), dimethyl carbonate (180 g, 2.0 mol) and a 28% sodium methoxide/methanol solution (1.3 g) were charged. The flask was heated to 120° C. to allow the starting materials to react for 10 hours while removing the methanol from the distillation columns by evaporation. After allowing the mixture to cool to room temperature, an aqueous solution of ammonium chloride was added to the mixture and the mixture was shaken to remove the sodium methoxide. The organic layer was washed with water, dried and distilled to give methyl 2,2,3,3,3-pentafluoropropyl carbonate as a colorless liquid (71 g, yield 51%). The chemical structure of the produced compound was determined based on the IR and NMR absorbance spectra shown in FIG. 7 and FIG. 8 respectively and the mass spectrometry spectrum (M/e=208).

The absorbance peaks of IR and NMR are shown below.

IR. (neat): 2964 (C-H), 1768 (C=O), 1447, 1402, 1377, 1354, 1290, 1203, 1155, 1105, 1048, 980, 786, 731, 642, 522 cm$^{-1}$ NMR (CDCl$_3$ soln., δppm): 3.86 (s, 3H, OCH$_3$), 4.59 (t, 2H, J=12.5 Hz, OCH$_2$CF$_2$CF$_3$)

The major physical properties are also shown in Table 1.

EXAMPLE 5

Synthesis of methyl 2,2,3,3-tetrafluoropropyl carbonate (the compound of the formula [I] where R$^1$=H and R$^2$=1,1,2,2-tetrafluoroethyl)

Figure 9:
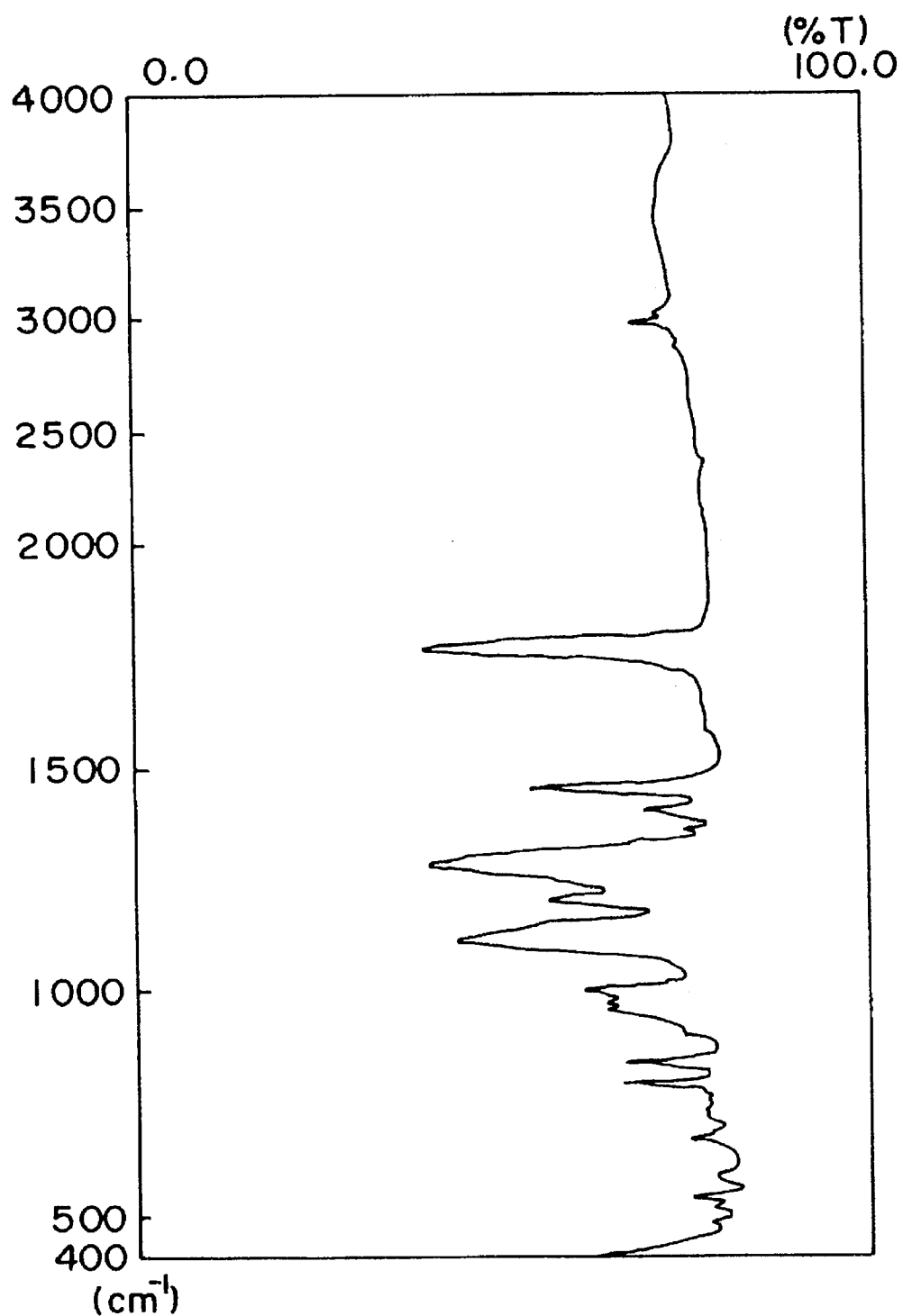
Figure 10:
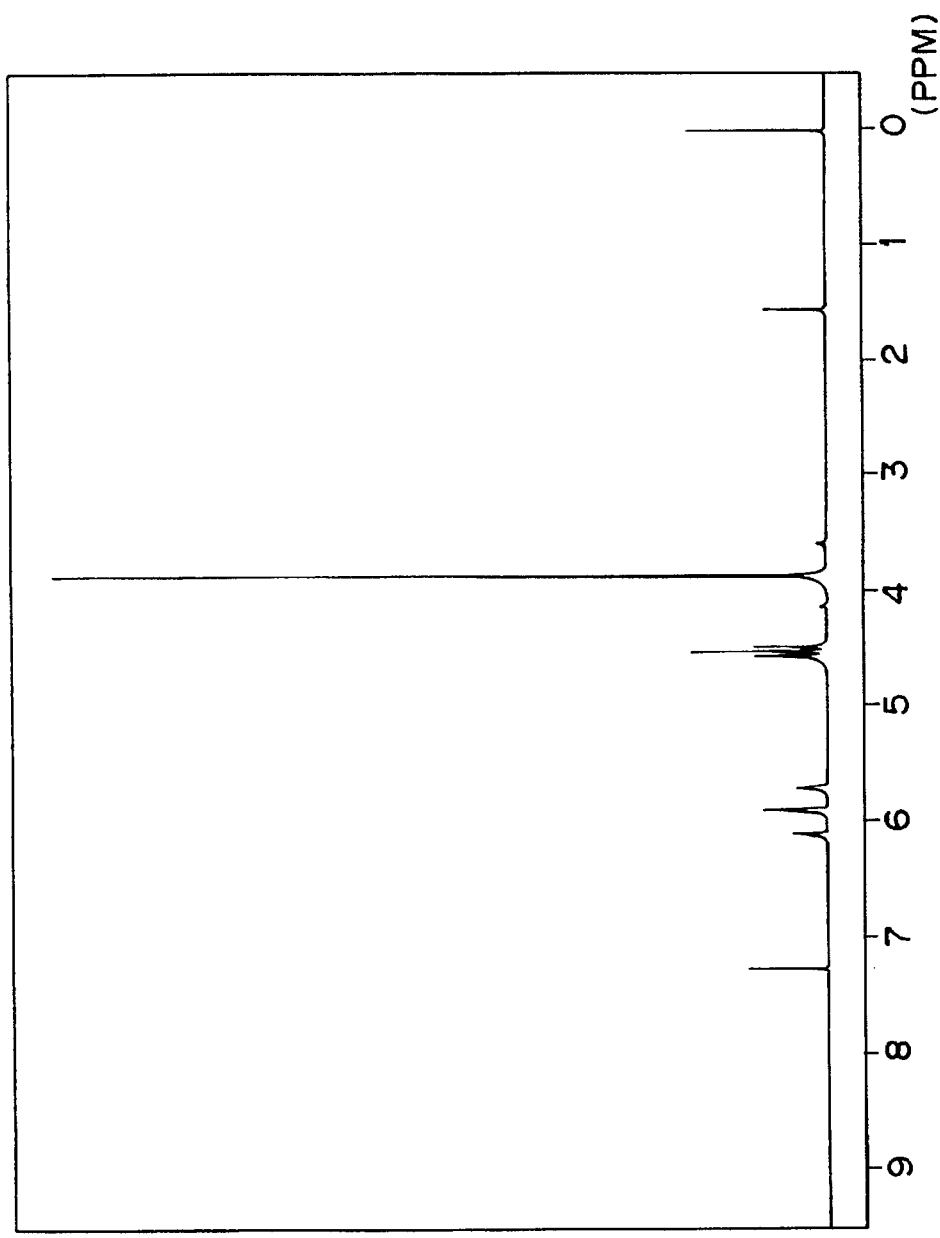

In a flask (500-ml volume) equipped with 10 distillation columns, 2,2,3,3-tetrafluoropropanol (100 g, 0.76 mol), dimethyl carbonate (205 g, 2.3 mol) and a 28% sodium methoxide/methanol solution (1.4 g) were charged. The flask was heated to 120° C. to allow the starting materials to react for 10 hours while removing the methanol from the distillation columns by evaporation. After allowing the mixture to cool to room temperature, an aqueous solution of ammonium chloride was added to the mixture and the mixture was shaken to remove the sodium methoxide. The organic layer was washed with water, dried and distilled to give methyl 2,2,3,3-tetrafluoropropyl carbonate as a colorless liquid (70 g, yield 49%). The chemical structure of the produced compound was determined based on the IR and NMR absorbance spectra shown in FIG. 9 and FIG. 10 respectively and the mass spectrometry spectrum (M/e= 190).

The absorbance peaks of IR and NMR are shown below.

IR (neat): 2964 (C-H), 1764 (C=O), 1446, 1396, 1277, 1204, 1106, 994, 834, 787, 662, 580, 534 cm$^{-1}$ NMR (CDCl$_3$ soln., δppm): 3.86 (s, 3H, OCH$_3$), 4.53 (t, 2H, J=12.5 Hz, OCH$_2$CF$_2$CF$_2$H), 5.90 (tt, 1H, J=53.1 Hz, H=4.3 Hz, OCH$_2$CF$_2$CF$_2$H)

The major physical properties are also shown in Table 1.

EXAMPLE 6

Synthesis of 2,2,2-trifluoroethyl 2,2,3,3,3-pentafluoropropyl carbonate (the compound of the formula [I] where R$^1$=trifluoromethyl and R$^2$=pentafluoroethyl)

First, in a flask (5-liter volume) equipped with 20 distillation columns, 2,2,2-trifluoroethanol (1000 g, 10.0 mol), dimethyl carbonate (1800 g, 20.0 mol) and a 28% sodium methoxide/methanol solution (15.3 g) were charged. Ater the flask was heated to 120° C. to allow the starting materials to react for 30 hours while removing the methanol from the distillation columns by evaporation, the flask was heated to 130° C. to allow the materials to react for 40 hours while removing the dimethyl carbonate from the distillation columns by evaporation. After allowing the mixture to cool to room temperature, an aqueous solution of ammonium chloride was added to the mixture and the mixture was shaken to remove the sodium methoxide. The organic layer was washed with water, dried and distilled to give di-2,2,2-trifluoroethyl carbonate as a colorless liquid (407 g, yield 36%).

Next, in a flask (500-ml volume) equipped with 10 distillation columns, 2,2,3,3,3-pentafluoropropanol (100 g, 0.76 mol), di-2,2,2-trifluoroethyl carbonate (520 g, 2.3 mol) thus obtained and a 28% sodium methoxide/methanol solution (1.4 g) were charged. The flask was heated to 120° C. to allow the starting materials to react for 10 hours while removing the 2,2,2-trifluoroethanol from the distillation columns by evaporation. After allowing the mixture to cool to room temperature, an aqueous solution of ammonium chloride was added to the mixture and the mixture was shaken to remove the sodium methoxide. The organic layer was washed with water, dried and distilled to give 2,2,2-trifluoroethyl 2,2,3,3,3-pentafluoropropyl carbonate as a colorless liquid (103 g, yield 40%). The chemical structure of the produced compound was determined based on the IR and NMR absorbance spectra and the mass spectrometry spectrum (M/e=276).

Figure 11:
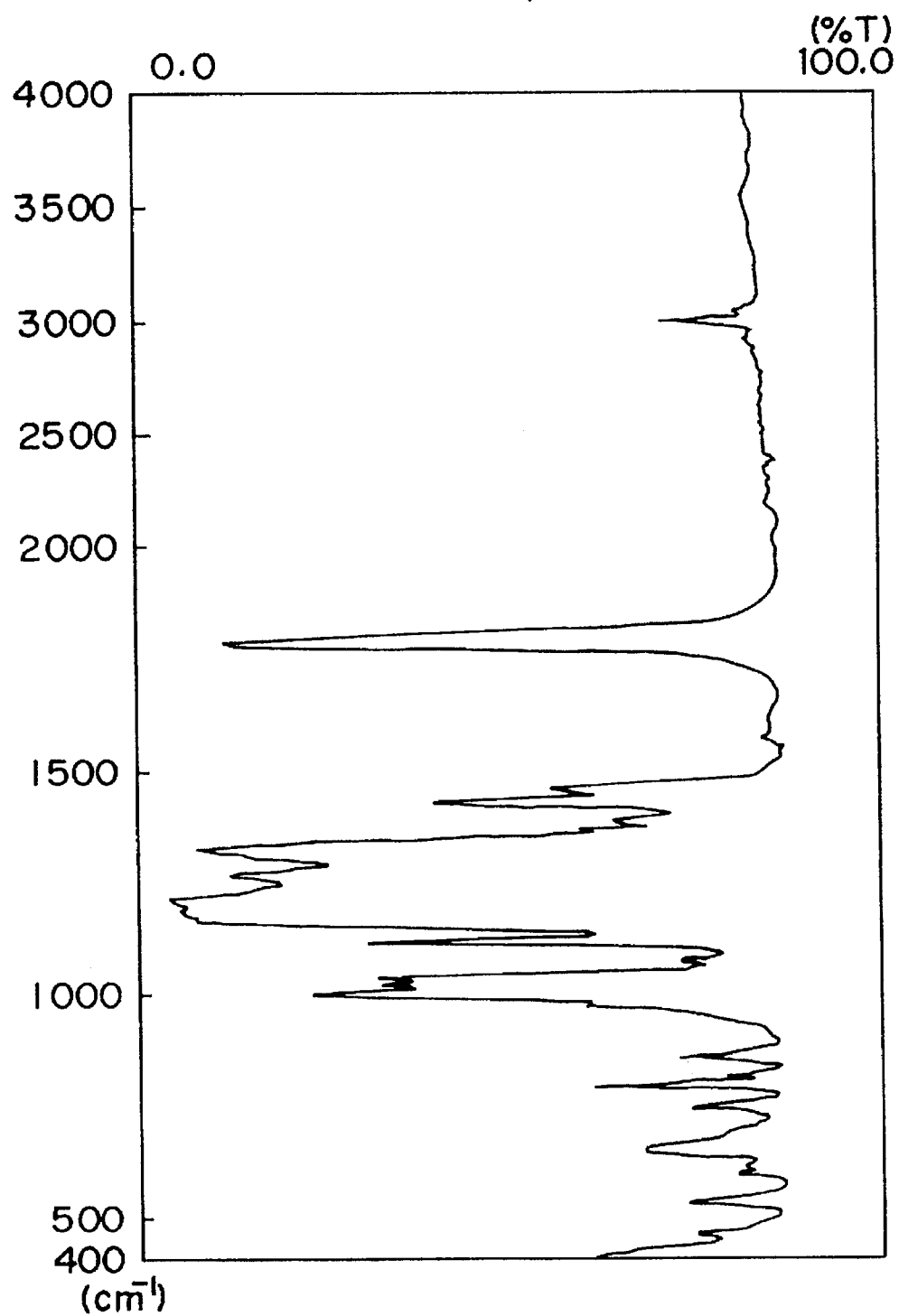
Figure 12:
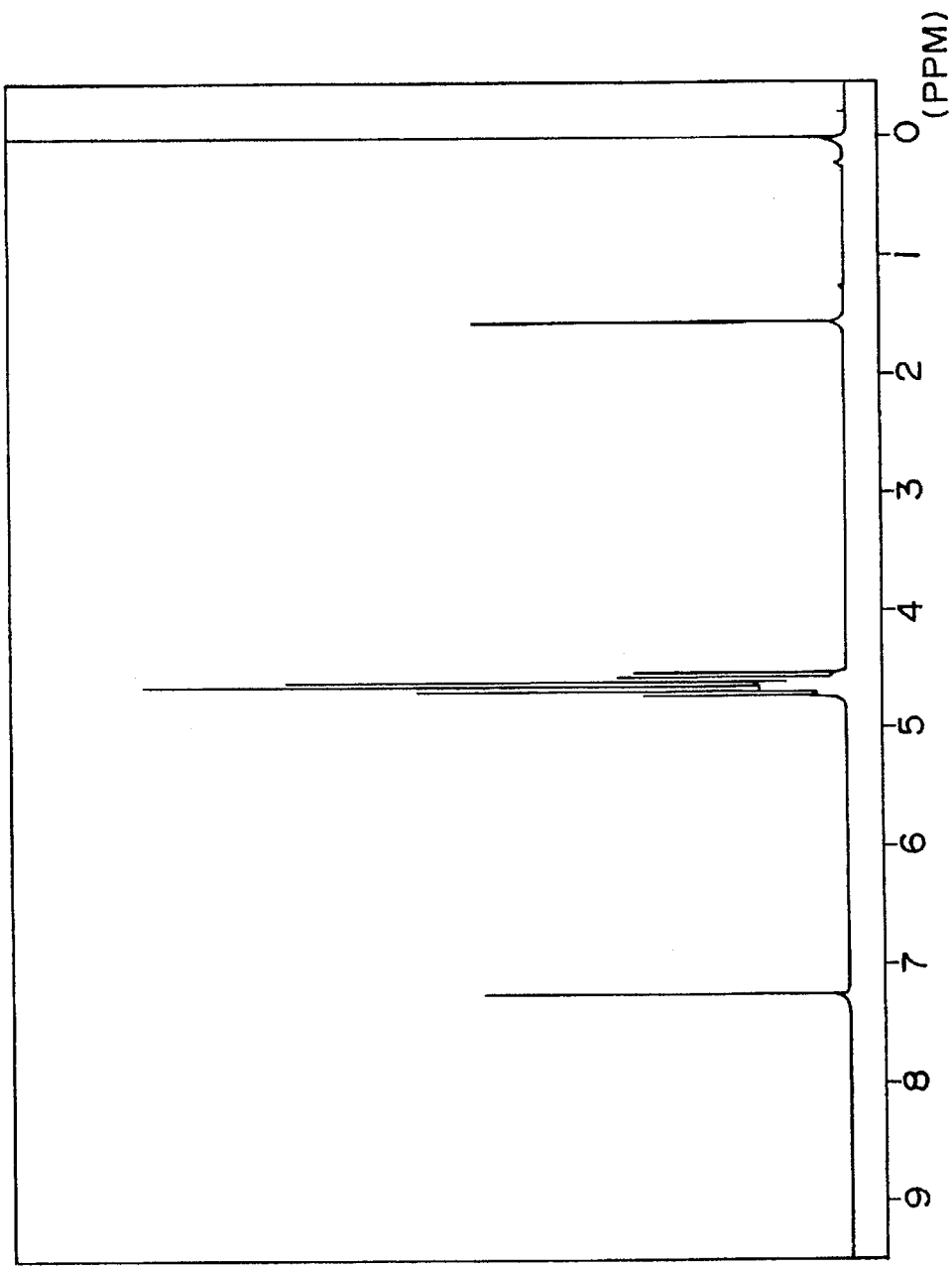

The absorbance peaks of IR and NMR shown in FIGS. 11 and 12 are shown below.

IR (neat): 2980 (C-H), 1782 (C=O), 1446, 1420, 1263, 1203, 1109, 991, 841, 781, 641, 522 cm$^{-1}$ NMR (CDCl$_3$ soln., δppm): 4.58 (q, 2H, J=8 Hz, OCH$_2$CF$_3$), 4.66 (t, 2H, J=13 Hz, OCH$_2$CF$_2$CF$_3$)

The major physical properties are also shown in Table 1. For reference, physical properties of dimethyl carbonate (Compound G), diethyl carbonate (Compound H), diisopropyl carbonate (Compound I) and di-2,2,2-trifluoroethyl carbonate (Compound J) are also shown in Table 1.

TABLE 1

| Example | Compound | Formula | Boiling Point (°C.) | Melting Point (°C.) | Viscosity cP (25° C.) | Specific Dielectric Constant (25° C.) |
|---|---|---|---|---|---|---|
| 1 | A | $CH_3OCOOCH_2C(CH_3)_3$ | 152–153 | 12 | 1.4 | 2.7 |
| 2 | B | $CH_3OCOOCH_2CF_3$ | 105–106 | –48 | 1.1 | 7.2 |
| 3 | C | $CH_3CH_2OCOOCH_2CF_3$ | 119–120 | –61 | 1.2 | 7.8 |
| 4 | D | $CH_3OCOOCH_2CF_2CF_3$ | 113–114 | –41 | 1.4 | 6.2 |
| 5 | E | $CH_3OCOOCH_2CF_2CF_2H$ | 145–146 | –100 | 3.0 | 8.8 |
| 6 | F | $CH_3CH_2OCOOCH_2CF_2CF_3$ | 126–127 | –110 | 2.2 | 5.9 |
|  | G | $CH_3OCOOCH_3$ | 91 | 3 | 0.6 | 2.6 |
|  | H | $CH_3CH_2OCOOCH_2CH_3$ | 123 | –43 | 0.7 | 2.8 |
|  | I | $(CH_3)_2CHOCOOCH(CH_3)_2$ | 145 | –38 | 1.3 | 2.5 |
|  | J | $CF_3CH_2OCOOCH_2CF_3$ | 114–115 | –39 | 1.7 | 7.5 |

As clearly seen from the results shown in Table 1, the carbonate compounds (A–F) of the present invention have a high boiling point and a low melting point, hence, a wide liquid state temperature range, and show a low viscosity. Therefore, the results Indicate that the compounds of the present invention are useful as solvents.

EXAMPLES 7

Methyl 2,2,3,3,3-Pentafluoropropyl carbonate was prepared by the same manner as the example 4 except that $K_2CO_3$ (0.046 g) was used as a catalyst in stead of a 28% sodium methoxide/methanol solution (1.3 g). After 2,2,3,3,3-pentafluoropropanol and dimethyl carbonate were allowed to react, the mixture thereof was passed through a column filled with silicagel (8 g) in order to remove $K_2CO_3$, and was distilled to give methyl 2,2,3,3,3-pentafluoropropyl carbonate as a colorless liquid (yield 55%).

EXAMPLES 8–13

Measurement of Flash Point

Flash points of each of the compounds (B, C, D and F) obtained in Examples 2, 3, 4 and 6 and a solution prepared by mixing the compound of Example 2 or 3 and propylene carbonate in a volume ratio of 1:1 were measured by the Tag closed method (ASTM D-56). As references, flash points of dimethyl carbonate (Compound G), di-2,2,2-trifluoroethyl carbonate (Compound J) and a solution prepared by mixing dimethyl carbonate and propylene carbonate In a volume ration of 1:1 were also measured. The results of the measurements are shown in Table 2.

TABLE 2

| Example | Sample | Flash Point (°C.) |
|---|---|---|
| 8 | Compound B | 37 |
| 9 | Compound C | 37 |
| 10 | Compound D | 46 |
| 11 | Compound F | >100 |
| 12 | Compound B + PC | 50 |
|  | Compound C + PC | 59 |
|  | Compound G | 22 |
|  | Compound G + PC | 24 |
|  | Compound J | >100 |

As seen from the results shown in the table above, the carbonate compounds of the present invention have a high flash point and therefore can be suitably used as solvents excellent in anti-oxidation properties.

EXAMPLES 14 AND 15

Reactivity with Metallic Lithium

Reactivity with metallic lithium was determined as to methyl neopentyl carbonate (Compound A) and methyl 2,2,2-trifluoroethyl carbonate (Compound B).

In an argon box, metallic lithium (0.1 g) cut into a cubic shape was added into methyl neopentyl carbonate (Compound A, 5 g) and the lithium was pushed with a spatula in the liquid to expose a clean surface of the lithium. After leaving at 25° C. for 48 hours, an appearance of the lithium surface and that of the liquid were examined to determine the reactivity of the solvent as compared with the initial state. The same experiments were carried out as to methyl 2,2,2-trifluoroethyl carbonate (Compound B) and the conventional compounds, diethyl carbonate (Compound H) and diisopropyl carbonate (Compound I), as references. The obtained results are shown in Table 3 below.

TABLE 3

| Example | Electrolyte Solvent | Reactivity with Li |
|---|---|---|
| 14 | Compound A | Not reacted |
| 15 | Compound B | Not reacted |
|  | Compound H | Reacted* |
|  | Compound I | Reacted* |

*The surface of the metal and the liquid turned into brown color.

As clearly shown by the results of Table 3, Compound A and Compound B did not react with metallic lithium and therefore they are extremely stable and suitable for electrolytic solution.

EXAMPLES 16–26

Measurements of Electro-conductivity and Decomposition Voltage

As an electrolyte, lithium hexafluorophosphate ($LiPF_6$, 3.8 g, 25 mmol) was dissolved In an electrolytic solution solvent to prepare 25 ml of 1 mol/liter electrolytic solution of $LiPF_6$. As the solvent, each of the carbonates synthesized above alone or a mixed solvent of each of the carbonates synthesized above and propylene carbonate (PC) (volume ratio=1:1) was used. Electro-conductivity of each electrolytic solution was determined by an impedance meter at 10 kHz. Further, decomposition voltage of each solution was measured by charging each solution in a three-electrode cell for voltage measurement equipped with platinum work and counter electrodes and metallic lithium reference electrode and performing voltage scanning at 50 mV/sec by means of a potentiostat. The voltage range where the electrolysis current of more than 0.1 mA does not flow was considered as the decomposition voltage. The results are shown in Table 4. The measurements were also performed as to PC alone and a mixed solvent of dimethyl carbonate and PC as references. The results are also shown in Table 4.

TABLE 4

| Example | Electrolyte Solvent ($LiPF_6$ = 1M/1) | Electro-conductivity (mS/cm) | Decomposition Voltage (V) |
|---|---|---|---|
| 16 | Compound A | 0.24 | 6.2 |
| 17 | Compound B | 1.7 | 6.3 |
| 18 | Compound D | 0.69 | 6.3 |
| 19 | Compound E | 0.59 | 6.3 |
| 20 | Compound A + PC | 4.2 | 6.3 |
| 21 | Compound B + PC | 5.7 | 6.3 |
| 22 | Compound C + PC | 4.8 | 6.3 |
| 23 | Compound D + PC | 3.6 | 6.3 |
| 24 | Compound E + PC | 3.5 | 6.3 |
| 25 | Compound F + PC | 3.6 | 6.3 |
| 26 | Compound J + PC | 3.2 | 6.3 |
|  | Compound G + PC | 10.7 | 5.6 |
|  | PC | — | 6.1 |

As clearly seen from the results of Tables 2 and 4, the electrolytic solutions of the present invention showed a high decomposition voltage and an excellent electro-conductivity of practically useful level. And these results show that they can be suitably used as an electrolyte solvent for batteries.

EXAMPLES 27 AND 28

Battery Life-time When Charge/discharge Cycle Was Repeated

Figure 13:
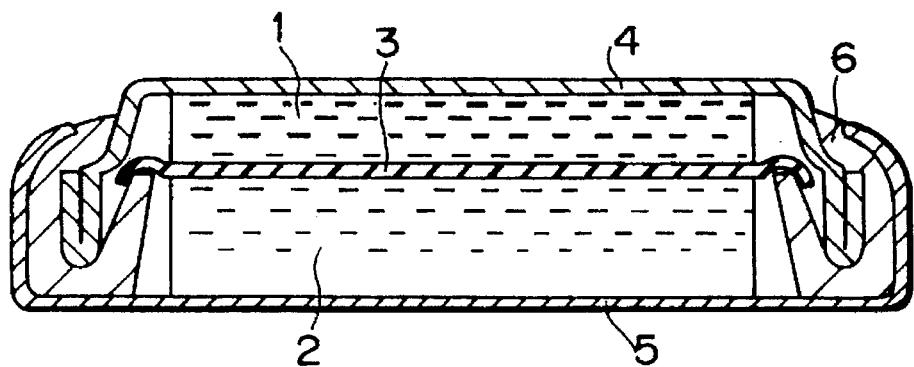
FIG. 13 shows one embodiment of the non-aqueous electrolyte battery according to the present invention. In the drawing, 1 represents anode and 2 represents cathode.

A non-aqueous electrolyte cell of coin-like shape such as shown In FIG. 13 having a diameter of 20 mm and a height of 2.5 mm was manufactured. The cell had a cathode 1 of metallic lithium and a anode 2 formed by pressure-molding of a mixture comprising 85 parts by weight of $LiCoO_2$, 12 parts by weight of graphite as a conductor and 3 parts by weight of fluorocarbon resin as a binder. The materials of the cathode 1 and the anode 2 were bonded to the cathode can 4 and anode can 5 via porous separator 3 made of polypropylene. An electrolytic solution of the cell was prepared by dissolving lithium hexafluorophosphate in a mixed solvent comprising methyl 2,2,2-trifluoroethyl carbonate (Compound B) and propylene carbonate (PC) in a volume ratio of 1:1 so that the solution have an electrolyte concentration of 1 mole/liter. The electrolyte was introduced into the cell from the sealing gasket 6 and sealed.

Thus manufactured cell was charged with a current of 1.0 mA and a maximum voltage of 4.1 V for 10 hours and then discharged with a current of 1.0 mA so that the cell showed a voltage of 3.0 V to determine the charge/discharge efficiency of the cell. Further, this charge/discharge cycle was repeated given times to determine the change of the charge/discharge efficiency of the cell. The results were shown in FIG. 14, where the charge/discharge efficiency is plotted to the number of cycles (o). The results obtained in the same manner as above as to a cell manufactured in the same way as used for the Compound B-PC system except that a mixed solvent of Compound A and PC (volume ratio=1:1) was used were also plotted in FIG. 14 (Δ). Further, the results obtained In a comparative coin-like shape cell manufactured In the same manner as the Compound B-PC system except that a mixed solvent of diethyl carbonate (Compound H) and propylene carbonate (volume ratio=1:1) was used as a electrolytic solution solvent were also plotted In FIG. 14 (●).

Figure 14:
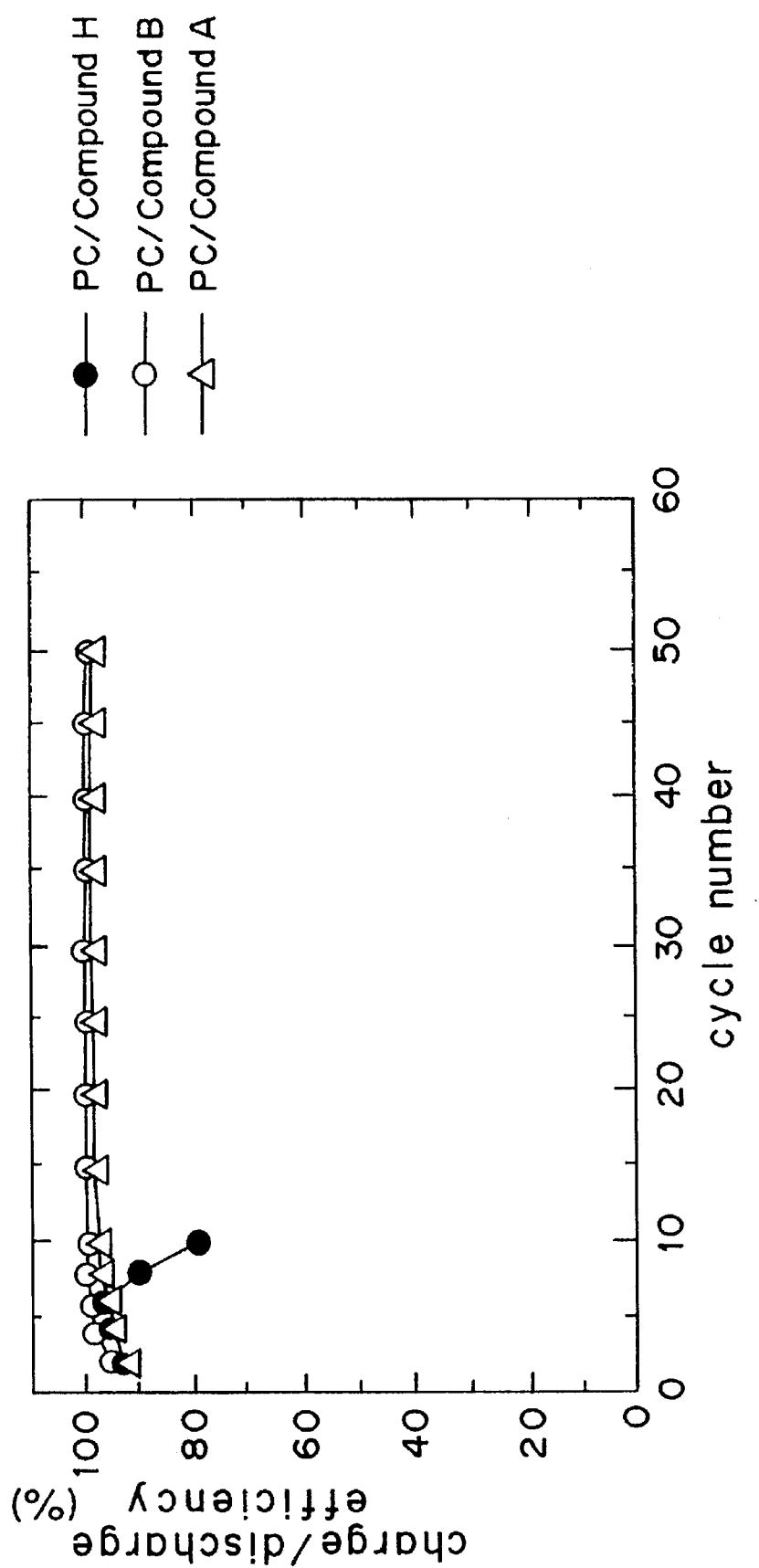
FIG. 14 shows charge/discharge cycle characteristics of the non-aqueous electrolyte battery according to the present invention.

As seen from the results shown in FIG. 14, the cell utilizing the electrolytic solution solvent of the present invention maintained high energy density even though it was subjected to a high voltage of more than 4 V, and showed extremely excellent cycle characteristics.

Advantages of the Invention

As clearly indicated by the examples described above, novel asymmetric carbonate compounds represented by the formula [II] where hydrogen atoms at the β-position of at least one alkyl group thereof are substituted are provided according to the present invention. These novel carbonate compounds are chemically and physically stable, have a low viscosity, high flash point and high dielectric constant, are capable of dissolving organic materials sufficiently and therefore useful as ordinary organic solvents, particularly as electrolyte solvents for batteries. Further, the novel carbonate compounds of the present invention, particularly when they contain halogen atoms In at least one alkyl group thereof, are excellent in flame retardant properties and hence can be used as flame-retardant solvents. The novel carbonate compounds of the present invention are, In addition to the use as solvents, useful as organic synthesis reagents, pharmaceuticals, agricultural chemicals, flame retardants and washing or cleaning agents.

As seen from the descriptions hereinbefore, according to the present invention, by using an organic solvent comprising the linear carbonates represented by the formula [II] as an electrolytic solution, there can be provided a non-aqueous electrolyte solution with high flash point, excellent electro-conductivity and decomposition voltage. Further, according to the present invention, by utilizing the non-aqueous electrolytic solution, there can be provided a battery with excellent charge/discharge characteristics and cycle characteristics as well as high energy density.

We claim:

1. A non-aqueous electrolytic solution comprising a carbonate compound represented by the general formula (II):

$$R^3\text{-O-CO-O-}R^4 \quad (II)$$

wherein $R^3$ represents an alkyl group or an alkyl group substituted by one or more halogen atoms, and $R^4$ represents an alkyl group having β-positioned carbon, and having no hydrogen atom at the β-position thereof or an alkyl group substituted by one or more halogen atoms and having no hydrogen atom at the β-position thereof.

2. The non-aqueous electrolytic solution of claim 1 wherein $R^3$ is an alkyl group or an alkyl group substituted by one or more fluorine atoms and $R^4$ is an alkyl group having no hydrogen atom at the β-position thereof or a fluorinated alkyl group having no hydrogen atom at the β-position thereof.

3. The non-aqueous electrolytic solution of claim 1 wherein $R^3$ is selected from the group consisting of —$CH_3$, —$CH_2CH_3$ and —$CH_2CF_3$, and $R^4$ is selected from the group consisting of —$CH_2C(CH_3)_3$, —$CH_2CF_3$, —$CH_2CF_2CF_3$, —$CH_2CF_2CF_2H$ and —$CH(CF_3)_2$.

4. The non-aqueous electrolytic solution of claim 1 where $R^3$ is —$CH_3$ and $R^4$ is —$CH_2CR_3$, wherein R represents an alkyl group, a halogenated alkyl group or halogen atom.

5. The non-aqueous electrolytic solution of claim 1 wherein $R^3$ is —$CH_3$ or —$CH_2CF_3$ and $R^4$ is —$CH_2CF_3$ or —$CH_2C(CH_3)_3$.

6. The non-aqueous electrolytic solution of claim 1 which comprises, in addition to the carbonate compound of the formula [II], a cyclic carbonate compound.

7. The non-aqueous electrolytic solution of claim 6 wherein the mixing volume ratio of the carbonate compound of the formula (II) and the cyclic carbonate compound ranges from 1:9 to 9:1.

8. The non-aqueous electrolytic solution of claim 1 wherein electrolyte is selected from the group of lithium compounds consisting of $LiPF_6$, $LiBF_4$, $LiClO_4$, $LiAsF_6$, $LiCF_3SO_3$, $LiAlCl_4$, $LiN(SO_2CF_3)_2$, $LiC_4F_9SO_3$ and $LiC_8F_{17}SO_3$.

9. A non-aqueous electrolyte battery comprising the non-aqueous electrolytic solution of claim 5.

10. A non-aqueous electrolytic solution comprising a carbonate compound represented by the formula (II):

$$R^3\text{-O-CO-O-}R^4 \qquad (II)$$

wherein $R^3$ represents an alkyl group having 1 to 5 carbon atoms or an alkyl group having 1 to 5 carbon atoms substituted by one or more halogen atoms, and $R^4$ represents an alkyl group having 5 to 8 carbon atoms and having no hydrogen atom at the β-position thereof or an alkyl group having 2 to 5 carbon atoms substituted by one or more halogen atoms and having no hydrogen atom at the β-position thereof.

11. The non-aqueous electrolytic solution of claim 10 wherein $R^3$ is an alkyl group having 1 to 5 carbon atoms or an alkyl group having 1 to 5 carbon atoms substituted by one or more fluorine atoms, $R^4$ is an alkyl group having 5 to 8 carbon atoms and having no hydrogen atom at the β-position thereof or a fluorinated alkyl group having 2 to 5 carbon atoms and having no hydrogen atom at the β-position thereof.

12. The non-aqueous electrolytic solution of claim 10 wherein $R^3$ is a member selected from the group consisting of —$CH_3$, —$CH_2CH_3$ and —$CH_2CF_3$, and $R^4$ is selected from the group consisting of —$CH_2C(CH_3)_3$, —$CH_2CF_3$—$CH_2CF_2CF_3$, —$CH_2CF_2CF_2H$ and —$CH_2(CF_3)_2$.

13. The non-aqueous electrolytic solution of claim 10 wherein $R^3$ is —$CH_3$ and $R^4$ is —$CH_2CR_3$, wherein R represents an alkyl group having one to two carbon atoms, a halogenated alkyl group having one carbon atom or fluorine atom.

14. The non-aqueous electrolytic solution of claim 10 wherein $R_3$ is —$CH_3$ or $CH_2CF_3$ and $R_4$ is —$CH_2CF_3$ or —$CH_2C(CH_3)_3$.

15. The non-aqueous electrolytic solution of claim 10 which comprises, in addition to the carbonate compound of the formula (II), a cyclic carbonate compound which is a member selected from the group consisting of ethylene carbonate, propylene carbonate, butylene carbonate and vinylene carbonate, at a ratio of the carbonate to cyclic carbonate of 8:2 to 2:8.

16. The non-aqueous electrolytic solution of claim 15 wherein the mixing volume ratio of the carbonate compound of the formula (II) and the cyclic carbonate compound is about 1:1.

17. The non-aqueous electrolytic solution of claim 10 wherein electrolyte is selected from the group of lithium compounds consisting of $LiPF_6$, $LiBF_4$, $LiClO_4$, $LiAsF_6$, $LiCF_3SO_3$, $LiAlCl_4$, $LiN(SO_2CF_3)_2$, $LiC_4F_9SO_3$ and $LiC_8F_{17}SO_3$.

18. A non-aqueous electrolyte battery comprising the non-aqueous electrolytic solution of claim 12.

19. A non-aqueous electrolytic solution comprising an electrolyte and a carbonate compound represented by the formula (II)

$$R^3\text{-O-CO-O-}R^4 \qquad (II)$$

wherein $R^3$ is a member selected form the group consisting of —$CH_3$, $CH_2CH_3$ and —$CH_2CF_3$ and $R^4$ is a member selected from the group consisting of —$CH_2C(CH_3)_3$ —$CH_2CF_3$, —$CH_2CF_2CF_3$, —$CH_2CF_2CF_2H$ and —$CH(CF_3)_2$, and the electrolyte is a member selected from the group of lithium compounds consisting of $LiPF_6$, $LiPF_4$, $LiClO_4$, $LAsF_6$, $LiCF_3SO_3$, $LiAlCl_4$, $LiN(SO_2CF_3)_2$, $LiCF_4F_9SO_3$ AND $LiC_8F_{17}SO_3$.

20. The non-aqueous electrolytic solution of claim 19 which comprises, in addition to the carbonate compound of the formula (II), a cyclic carbonate compound which is a member selected from the group consisting of ethylene carbonate, propylene carbonate and butylene carbonate, at a ratio of carbonate to cyclic carbonate of 8:2 to 2:8.

21. The non-aqueous electrolytic solution of claim 19 wherein $R^3$ is —$CH_3$ or —$CH_2CF_3$ and $R_4$ is —$CH_2CF_3$ or —$CH_2C(CH_3)_3$.

22. The non-aqueous electrolytic solution of claim 20 wherein the mixing volume ratio of the carbonate compound of the formula (II) and the cyclic carbonate compound is about 1:1.

23. The non-aqueous electrolytic solution of claim 19 wherein $R^3$ is —$CH_2CF_3$ and $R_4$ is a member selected from the group consisting of —$CH_2CF_3$, —$CH_2CF_2CF_3$, —$CH_2CF_2CF_2H$, and —$CH(CF_3)_2$.

24. A non-aqueous electrolyte battery comprising the non-aqueous electrolytic solution of claim 20.

* * * * *